United States Patent [19]

Stringfellow

[11] 4,092,425

[45] May 30, 1978

[54] RESTORATION OF INTERFERON RESPONSE

[75] Inventor: Dale A. Stringfellow, Kalamazoo, Mich.

[73] Assignee: The Upjohn Company, Kalamazoo, Mich.

[21] Appl. No.: 822,742

[22] Filed: Aug. 8, 1977

[51] Int. Cl.[2] .................. A61K 31/215; A61K 31/19; C12K 9/00

[52] U.S. Cl. .................................. 424/305; 195/1.8; 424/317

[58] Field of Search ................. 424/305, 317; 195/1.8

[56] References Cited

PUBLICATIONS

Plescia et al–Chem. Abst., vol. 85 (1976) p. 141040e.

*Primary Examiner*—Sam Rosen

*Attorney, Agent, or Firm*—William G. Jameson; Sidney B. Williams, Jr.

[57] ABSTRACT

The present invention provides a method for treatment of hyporeactivity to interferon induction in interferon producing animals or animal cells which comprises administering a hyporeactive interferon stimulating prostaglandin (HIS-PG) to an interferon producing animal or animal cells having a hyporeactive (decreased) interferon response. Hyporeactive interferon stimulating prostaglandins (HIS-PG) refers to those prostaglandin-type compounds which are useful in alleviating the decreased ability of interferon producing animals or animal cells to produce interferon following administration of repeated doses of an interferon inducer or as a consequence of viral infection or neoplasia.

35 Claims, No Drawings

RESTORATION OF INTERFERON RESPONSE

BACKGROUND OF THE INVENTION

It has previously been demonstrated that virus infected animals progressively lose their ability to respond to interferon induction, see D. A. Stringfellow and L. A. Glasgow, Hyporeactivity of infection: Potential limitation to therapeutic use of interferon-inducing agents, *Infect. Immum.*, 6: 743 (1972); J. E. Osborn and D. N. Medearis, Suppression of Interferon and Antibody and Multiplication of Newcastle Disease Virus in Cytomegalovirus Infected Mice, Proc. Soc. Exp. Biol. Med., 124: 347 (1967); D. A. Stringfellow, Inducer dependent State of Hyporeactivity Created by Infection, 14th Interscience Conf. Antimicrob. Agents Chemother, Abst. 136, (1974) O. A. Holtermann and E. A. Havell, Reduced interferon response in mice congenially infected with lymphocytic-choriomeningitis virus, J. Gen. Viro, 9: 101 (1970) and D. A. Stringfellow et al., Suppressed Response to Interferon Induction in Mice Infected with Encephalomyocarditis, Semliki Forest, $A_2$ Influenza, Herpes Hominis Type 2 or Murine Cytomegalo Viruses, J. Infect. Dis., 135:540 (1977). Also, animals exposed to repeated doses of various interferon inducers have been reported to develop a hyporeactive interferon response, see Buckler, C. E., DuBuy, H. G., Johnson, M. L., and Baron, S. 1971. Kinetics of serum interferon response in mice after single and multiple injections of Poly I; poly C. Proc. Soc. Exp. Biol. Med. 136: 394–398., Colby, C., and Morgan, M. J. 1971. Interferon induction and action. Annu. Rev. Microbiol. 25:333–360., Ho, M. and Kono, Y. 1965. Tolerance to the induction of interferons by endotoxin and virus. J. Clin. Invest. 44: 1059–1060, Park, J. K. and Baron, S. 1968. Herpetic keratoconjunctivitis therapy with synthetic double-stranded RNA. Science 1628:811–813, Vilcek, J. 1969. Interferon, pp. 42. In Virology Monographs. Springer Verlag. New York., Vilcek, J. and Rada, B. 1962. Studies on an interferon from tickborne encephalitis virus infected cells. III Antiviral action on interferon. Acta. Virol. 6:9–16, Youngner, J. S. and Stinebring, W. R. 1965. Interferon appearance stimulated by endotoxin, bacteria or viruses in mice pretreated with Esherichia coli endotoxin or infected with *Mycobacterium tuberculosis*. Nature (London) 208:456–458, Stringfellow, D. A. and Glasgow, L. A., tilorone hydrochloride: An oral interferon-inducing agent. *Antimicrob. Agents Chemother* 2, 73–78. Stringfellow, D. A. comparative interferon inducing and antiviral properties of 2-amino-5-bromo-6-methyl-4-pyrimidinol (U-25,166), tilorone HCL and Poly I:C. 16th Interscience Conference on Antimicrobial Agents and Chemotherapy. Abstract 128B-1976.

The use and effect of $PGE_1$, on the ability of various cells and mice to produce interferon in response to interferon inducers is described by Mécs, I. and Maraz, A. in Advances in the Biosciences, 9:453 (1972) and by Mécs et al. in Acta Microbiologica Academiae Scientiarum Hunqaricae, 21:265 (1974). However, Mécs et al. does not disclose or suggest that the administration of $PGE_1$ to cells or animals with a hyporeactive interferon response will restore their ability to respond to interferon inducers.

Both naturally occuring prostaglandins and prostaglandin analogs are known in the art. The naturally occuring prostaglandins have the prostanoic acid skeleton, and carbon atom numbering illustrated by Formula I:

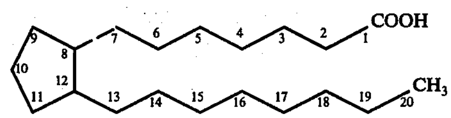

See Bergstrom, et al. Pharmacol. Rev. 20, 1 (1968) and references cited therein. For example, prostaglandin $E_2$ ($PGE_2$) exhibits the following structure:

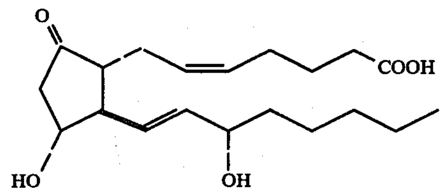

The term prostaglandin analog herein refers to those compounds structurally related to the prostaglandins (in that they exhibit a cyclopentane, or adjacently homologous cycloalkane, ring and a pair of side chains attached to adjacent carbon atoms of the ring) which retain characteristic biological properties of the prostaglandins. See Bergstrom, cited above. Various structural modifications of the prostaglandins are known to produce useful prostaglandin analogs. For example, the replacement of the carboxy with a hydroxymethyl or aminomethyl is known; substitution of a methyl, ethyl, or fluoro for a hydrogen at, for example, C-2 or C-16, and replacement of a methylene by an oxa or thia at, for example, C-5 is known. Further, partially deoxygenated prostaglandins are known to be useful prostaglandin analogs. Accordingly, 9-deoxy, 11-deoxy, and 15-deoxy-prostaglandins are known. Further, there are known prostaglandin analogs wherein the double bonds of, for example, $PGF_{2\alpha}$ are shifted, e.g., cis-4,5-didehydro-$PGF_{1\alpha}$, or replaced by triple bonds, e.g., 13,14-didehydro-$PGF_{2\alpha}$. Finally there are known bicyclic large ringed lactones wherein the C-1 carboxyl forms a lactone with a ring or side chain hydroxyl, at C-9, C-11, or C-15.

As used herein, the term prostaglandin-type compound refers to any prostaglandin or prostaglandin-analog including the carboxylate esters and pharmaceutically acceptable salts thereof.

Among the known prostaglandins are those referred to as A-type prostaglandins, E-type prostaglandins, F-type prostaglandins and D-type prostaglandins by those of skill in the art. The A-type prostaglandins, characterized by a double bond between carbon atoms 10 and 11 in the cyclopentane ring and a keto group at the 9 position, include prostaglandin $A_1$, or $PGA_1$, prostaglandin $A_2$ or $PGA_2$, prostaglandin $A_3$ or $PGA_3$, and dihydro prostaglandin A, or dihydro $PGA_1$. Similarly, the E-type prostaglandins with a keto group at the 9 position include $PGE_1$, $PGE_2$, $PGE_3$, and dihydro $PGE_1$, while the F-type prostaglandins with hydroxyl groups at the 9 and 11 positions include $PGF_{1\alpha}$, $PGF_{2\alpha}$, $PGF_{3\alpha}$ and dihydro $PGF_{1\alpha}$. The α-designation shows the configuration of the hydroxyl group at the 9 position in the cyclopentane ring. The D-type prostaglandins characterized by a keto group in the 11 position and an α hydroxyl group in the 9 position of the cyclopentane ring, include prostaglandin $D_1$ or $PGD_1$, prostaglandin $D_2$ or $PGD_2$, prostaglandin $D_3$ or $PGD_3$ and dihydro prostaglandin $D_1$ or dihydro $PGD_1$, and are described in Foss, P. S., Sih, C. J., Takeguchi, C. and Schnoes., H. (1972) Biosynthesis and Chemistry of $9\alpha$,15(S)-Dihydroxy-11-oxo-13-trans-prostenoic Acid. Biochemistry 11, 2271–2277 as well as U.S. Pat. Nos. 3,767,813 and 4,016,184.

As used herein, the term A-type prostaglandin refers to the A-type prostaglandin or any prostaglandin-analog thereof. The term E-type prostaglandin refers to the E-type prostaglandin or any prostaglandin-analog thereof. The term F-type prostaglandin refers to the F-type prostaglandin or any prostaglandin-analog thereof. The term D-type prostaglandin refers to the D-type prostaglandin or any prostaglanin-analog thereof.

Among the A-type, E-type, F-type and D-type prostaglandin compounds to be used according to this invention are the free acid form, the salt form wherein the cation is pharmaceutically acceptable, and the ester form wherein the alcohol portion is alkyl, especially alkyl of one to four carbon atoms, inclusive, more especially methyl or ethyl.

SUMMARY OF THE INVENTION

The present invention provides a method for alleviating a hyporeactive interferon response in interferon producing animals or cells having a hyporeactive interferon response which comprises administering to said animal or cells an effective amount of a hyporeactive interferon stimulating prostaglandin (HIS-PG) to alleviate said hyporeactive state.

The present invention relates to interferon formation and the restoration of the interferon response in interferon producing animals or cells having a hyporeactive (decreased) interferon response. Accordingly, the present invention includes the administration of hyporeactive interferon stimulating prostaglandins (HIS-PG's) in conjunction with suitable interferon inducers at times when interferon responsiveness is suppressed, due to virus infection, repeated doses of inducer, or neoplasia, to enhance the host's interferon response to the inducer. The present invention also includes the administration of hyporeactive interferon stimulating prostaglandins (HIS-PG's) without inducers to virus infected animals to enhance the interferon responses of the host towards the invading virus.

Further, as indicated, the present invention includes the administration of hyporeactive interferon stimulating prostaglandins (HIS-PG's) in in vitro processes designed to mass produce large quantities of interferon for clinical use. HIS-PG's can be used to enhance the interferon responsiveness of hyporeactive interferon-producing human or animal cells.

The term "interferon-producing human or animal cells" as used throughout the specification and claims means cells isolated from humans or animals, which cells are capable of being stimulated with an interferon inducer to produce interferon in vitro. Example of such cells are cells isolated from embryos and fetuses, or from organs and tissues (such as foreskin, amnion, kidney, thyroid), leucocytes, various cell strains such as the human diploid cell strain known to the art as WI-38, and transformed cell lines such as Hela.

The term "in vitro" as used throughout the specification means cells isolated, grown or treated as stationary cultures (e.g, tissue culture dishes), as non-stationary cultures (e.g., roller bottles and microcarriers), or as suspensions.

Those prostaglandin-type compounds effective for the present purpose are the hyporeactive interferon stimulating prostaglandins (HIS-PG's), which are herein defined to be those prostaglandin-type compounds known in the art which are at least 0.1 times or 10% as active as $PGE_1$ in a laboratory assay described in Procedure I for determining the ability of prostaglandin-type compounds to increase the interferon response in animals or cells having a hyporeactive (decreased) interferon response. Accordingly, any prostaglandin-type compound exhibiting at least 10% of the potency of $PGE_1$ in the assay described in Procedure I represents a HIS-PG. Contemplated as especially preferred for the present purpose are HIS-PG's wherein the potency in Procedure I is at least 25 percent of the potency of $PGE_1$.

Examples of prostaglandin-type compounds which can be used as HIS-PG's are:

$PGE_1$
$PGA_1$
$PGF_{1\alpha}$
$PGE_2$
$PGA_2$
$PGF_{2\alpha}$
Cis-4,5-didehydro-15-methyl-$PGE_1$ methyl ester.

The above HIS-PG's are all named essentially according to the system of nomenclature described by Nelson, J. Med. Chem. 17:911 (1974).

With regard to the above list of HIS-PG's , various known pharmacologically acceptable salts are used in place of the free acids or methyl esters enumerated above. Examples of such known salts are those with pharmaceutically acceptable metal cations, ammonium or amine cations, quaternary ammonium cations, and basic amino acid cations.

See especially, those salts described for use with the prostaglandins in U.S. Pat. No. 4,016,184.

When administering HIS-PG's to an intact (whole) animal, the present invention requires the use of an amount of HIS-PG which is effective to alleviate the hyporeactive interferon response. For this purpose a wide variety of dosage schedules and routes of administration can be employed. The dosage regimen for the HIS-PG in accord with this invention will depend upon a variety of factors, including the type, age, weight, sex, and physical condition of the interferon producing animal, the nature and dosage regimen of any interferon inducers being administered, the relative ability of the animal to respond to interferon induction, and the particular HIS-PG to be administered. If the HIS-PG is to be administered to bolster host interferon response to a virus infection independent of interferon inducer; dosage, time and frequency of administration will depend upon the virus infection being treated.

The HIS-PG is administered as a single dosage unit or in a treatment regimen of divided dosage units. However, the treatment is repeated, as needed, if a hyporeactive interferon response reoccurs. For convenience, the treatment can be given with each additional administration of inducer.

It is within the skill of the attending physician or veterinarian to determine the presence of a hyporeactive (decreased) interferon response utilizing established analysis procedures, and to prescribe an effective amount of the HIS-PG to alleviate the hyporeactive interferon response. In doing that, the physician or veterinarian would by one method start at a relatively low dose of the HIS-PG. For example, about 0.001 mg./kg. to about 0.5 mg./kg., and observe the response of the human or animal for 1-2 days. The dose of the HIS-PG is then adjusted downward or upward until the minimum effective dose is established. For any human or animal the dosage can be varied within a wide range when in the opinion of the attending physician or veterinarian the human or animal is receiving too little PG (i.e., restoration of the interferon response is unsuccessful) or too much PG (i.e., side effects, notably diarrhea and vomiting, are too intense or too prolonged after administration). The maximum needed dose is usually between about 0.01 mg./kg. and about 0.001 mg./kg. Once the minimum effective dose of the particular hyporeactive interferon stimulating prostaglandin (HIS-PG) is determined for a particular subject it is advantageous to provide the subject with a dosage schedule which will provide a substantially uniform level of interferon responsiveness.

Effective dosage of the HIS-PG depends upon the potency of the particular HIS-PG relative to $PGE_1$, for which doses in the range of about 1 mg./kg. to about 0.001 mg., more particularily about 0.1 mg./kg. to about 0.001 mg./kg. can be employed for parenteral administration. For HIS-PG's other than $PGE_1$ the parenteral dose should not exceed 100 times the maximum dose of $PGE_1$ indicated above.

The HIS-PG's in an effective therapeutic amount are administered in pharmaceutical preparations formulated for administration, including for example, oral, parenteral, intranasal and rectal administration.

Oral pharmaceutical preparations include both solid and liquid dosage forms.

Parenteral administration includes intravenous, subcutaneous, intramuscular, and the like.

Pharmaceutical preparations for nasal administration include sprays formulated with acceptable aqueous means, for example, a buffered isotonic aqueous vehicle containing appropriate buffer salts.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or non-aqueous.

Pharmaceutically acceptable substances utilized in parenteral preparations include aqueous vehicles, non-aqueous vehicles, antimicrobial agents, isotonic agents, buffers, antioxidants, local anesthetics, suspending and dispersing agents, emulsifying agents, sequestering or chelating agents and other pharmaceutical necessities.

Examples of aqueous vehicles include Sodium Chloride Injection, Ringer's Injection, Isotonic (5 percent) Dextrose Injection, Sterile Water for Injection, Dextrose and Sodium Chloride Injection and Lactated Ringer's Injection. Non-aqueous parenteral vehicles include fixed oils of vegetable origin, for example, cottonseed oil, corn oil, sesame oil and peanut oil. Antimicrobial agents in bacteriostatic or fungistatic concentrations must be added to parenteral preparations packaged in multiple-dose containers (vials) which include phenol or cresols, mercurials, benzyl alcohol, chlorobutanol, methyl, and propyl p-hydroxybenzoic acid esters, thimerosal, benzalkonium chloride and benaethonium chloride. Isotonic agents include, for example, sodium chloride and dextrose. Buffers include, for example, phosphate and citrate. Antioxidants include, for example, sodium bisulfite. Local anesthetics include, for example, procaine hydrochloride. Suspending and dispersing agents include, for example, sodium carboxymethylcellulose, hydroxypropyl methylcellulose and polyvinylpyrrolidone. Emulsifying agents include, for example, Polysorbate 80 (Tween 80). A sequestering or chelating agent of metal ions include for example, EDTA (ethylenediaminetetraacetic acid). Pharmaceutical necessities include, for example, ethyl alcohol, polyethylene glycol and propylene glycol for water miscible vehicles and sodium hydroxide, hydrochloric acid, citric acid, or lactic acid for pH adjustment.

The concentration of the pharmaceutically active ingredient is adjusted so that an injection, for example, 0.5 ml., 1.0 ml., 2.0 ml. and 5.0 ml. or an intravenous infusion, for example, 0.5 ml./min., 1.0 ml./min., 1.0 ml./min. provides an effective amount to produce the desired pharmacological effect. The exact dose depends on the age, weight, and condition of the patient or animal as is known in the art.

The unit-dose parenteral preparations are packaged, for example, in an ampule or a syringe with a needle. The multiple-dose package, for example, is a vial.

All preparations for parenteral administration must be sterile, as is known and practiced in the art.

Illustratively, intravenous infusion of a sterile aqueous solution containing a prostaglandin analog is an effective mode of administration. Another embodiment is a sterile aqueous or oily solution or suspension containing a prostaglandin analog injected as necessary to produce the desired pharmacological effect.

Oral pharmaceutical dosage forms are either solid or liquid. The solid dosage forms are tablets, capsules, granules and bulk powders. Types of oral tablets are, for example, compressed (including chewable and lozenge), tablet triturates, enteric-coated, sugar-coated, film-coated, and multiple compressed. Capsules are either hard or soft elastic gelatin. Granules and powers are either effervesent or non-effervescent.

Pharmaceutically acceptable substances utilized in compressed tablets are binders, lubricants, diluents, disintegrating agents, coloring agents, flavoring agents, flow inducing agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which ususally four different layers of pharmaceutically acceptable substances have been applied. Film-coated tablets are compressed tablets which have been coated with a water soluble cellulose high polymer. Multiple compressed tablets are compressed tablets made by more than one compression cycle utilizing the pharmaceutically acceptable substance previously mentioned. Coloring agents are utilized in all the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Examples of binders include glucose solution (25-50%), acacia mucilage (10-20%), gelatin solution (10-20%), sucrose and starch paste. Lubricants include, for example, talc, starch, magnesium or calcium stearate, lycopodium and stearic acid. Diluents include, for example, lactose, sucrose, starch, kaolin, salt, mannitol, and dicalcium phosphate. Disintegrating agents include, for example, corn starch, potato starch, bentonite, methylcellulose, agar, and carboxymethylcellulose. Coloring agents include, for example, any of the approved certified water soluble FD and C dyes, mixtures thereof, and water insoluble FD and C dyes suspended on alumina hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate, and polyoxyethylene laural ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets include, for example, dextrin and gelatin. The second layer, an opaque zone, includes, for example, starch, talc, calcium carbonate, magnesium oxide, and magnesium carbonate. The third layer, a translucent zone, includes, for example, sucrose. The fourth layer, a glaze, includes, for example, beeswax, carnauba wax, or a mixture of these waxes. Film coatings include, for example, hydroxyethylcellulose, sodium carboxymethylcellulose, polyethylene glycol 4000 and cellulose acetate phthalate.

Hard gelatin capsules, sizes 5 through 000. are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastrointestinal tract, polyvinyl alcohol, ethyl cellulose, and mixtures of beeswax, carnauba wax or bayberry wax with glyceryl monostearate.

Soft elastic gelatin capsules contain sufficient glycerin so that they are permanently flexible. Pharmaceutically acceptable liquid diluents used in soft elastic gelatin capsules are those which do not dissolve or harm the capsule and which are non-toxic, including, for example, corn oil, cottonseed oil, and polysorbate 80.

Pharmaceutically acceptable substance utilized in non-effervescent granules, for solution and/or suspension, include diluents, wetting agents. Flavoring agents, and coloring agents. Examples of diluents, wetting agents, flavoring agents and coloring agents include those previously exemplified.

Pharmaceutically acceptable substance utilized in effervescent granules and powders include organic acids, a source of carbon dioxide, diluents, wetting agents, flavoring agents, and coloring agents.

Examples of organic acids include, for example, citric acid and tartaric acid. Sources of carbon dioxide include, for example, sodium bicarbonate and sodium carbonate. Examples of sweetening agents include, for example, sucrose, calcium cyclamate and saccharin. Examples of diluents, wetting agents, and coloring agents include those previously exemplified.

Bulk powders have the prostaglandin analog uniformly dispersed throughout a pharmaceutically acceptable powdered carrier diluent. Examples of the diluent include those previously exemplified.

The individual oral solid pharmaceutical dosage forms, tablets and capsules, are packaged individually, unit dose, or in quantity, multiple dose containers, for example, bottles of 50, 100, 500, 1,000, or 5,000.

The amount of prostaglandin analog per dosage unit (tablet or capsule) is adjusted so that a tablet or capsule, a fraction or multiple thereof, provides the patient with an effective amount. The exact dose depends on the age, weight and condition of the patient or animal as is known in the art. Tablets and capsules are given in sufficient number and frequency to obtain the desired pharmacological effect.

The sustained release tablets and capsules provide an effective amount upon ingestion and continue to release a sufficient amount of the prostaglandin analog to keep the concentration of the prostaglandin analog at an effective level for increased periods of time, for example, 12 hours.

Non-effervescent granules and powders are packaged in predetermined amounts, such that when reconstituted with a specified quantity of an appropriate liquid vehicle, usually distilled water, a solution and/or suspension results, providing a uniform concentration of the prostaglandin analog, after shaking, if necessary. The concentration of the solution is such that a teaspoonful (5 ml.) a tablespoonful (one-half ounce or 15 ml.) or a fraction or a multiple thereof, will provide an effective amount to produce the desired pharmacological effect. The exact dose depends on the age, weight, and condition of the patient or animal, as is known in the art.

Effervescent granules and powders are packaged either in unit-dose, for example, metal foil packets, or in bulk, for example, in 4 oz. and 8 oz. amounts, such that a specific amount, either a unit-dose or, for example, a teaspoonful, tablespoonful, or a fraction or a multiple thereof of bulk granules, when added to a specific amount of liquid vehicle, for example, water, yields a container of liquid dosage form to be ingested. The concentration of the prostagandin analog in the granules is adjusted so that a specified amount when mixed with a specific amount of water yields an effective amount of the prostaglandin analog and produces the desired pharmacological effect. The exact amount of granules to be used depends on age, weight, and condition of the patient as is known in the art.

Liquid oral dosage forms include, for example, aqueous solutions, emulsions, suspensions and/or suspensions reconstituted from non-effervescent granules and effervescent preparations reconstituted from effervescent granules. Aquesous solutions include, for example, elixirs and syrups. Emulsions are either oil in water (o/w) or water-in-oil (w/o).

Elixirs are clear, sweetened, hydroalcoholic preparations. Pharmaceutically acceptable substances utilized in elixirs include, for example, solvents. Syrups are concentrated aqueous solutions of a sugar, for example, sucrose, and may contain a preservative. An emulsion is a two-phase system in which one liquid is dispersed in the form of small globules throughout another liquid, o/w emulsions are much preferred for oral administration over w/o emulsions. Pharmaceutically acceptable substances utilized in emulsions are non-aqueous liquids, emulsifying agents and preservatives. Suspensions utilize pharmaceutically acceptable suspending agents and preservatives. Pharmaceutically acceptable substances utilized in non-effervescent granules, to be reconstituted into a liquid oral dosage form, include, for example, diluents, sweeteners, and wetting agents. Pharmaceutically acceptable substances utilized in effervescent granules to be reconstituted into a liquid oral dosage form, include, for example, organic acids and a source of carbon dioxide. Coloring and flavoring agents are utilized in all of the above dosage forms.

Solvents include, for example, glycerin, sorbitol, ethyl alcohol, and syrup. Examples of preservatives include glycerin, methyl and propylparaben, benzoic acid, sodium benzoate, and alcohol. Examples of non-aqueous liquids utilized in emulsions include, for example, mineral oil, and olive oil. Examples of emulsifying agents include for example, gelatin, acacia, tragacanth, bentonite, and surfactants such as polyoxyethylene sorbitan monooleate. Suspending agents include, for example, sodium carboxymethylcellulose, pectin, tragacanth, Veegum, and acacia. Diluents include, for example, lactose and sucrose. Sweetening agents include, for example, sucrose, syrups, glycerin, and artificial sweetening agents such as sodium cyclamate and saccharin. Wetting agents include, for example, propylene glycol monostearate, sorbitan monooleate, diethylene glycol monolaurate and polyoxyethylene lauryl ether. Organic acids include, for example, citric and tartaric acid. Sources of carbon dioxide include, for example, sodium bicarbonate and sodium carbonate. Coloring agents include, for example, any of the approved certified water soluble FD and C dyes, and mixtures thereof. Flavoring agents include, for example, natural flavors extracted from plants such as fruits, and synthetic blends of compounds which produce a pleasant taste sensation.

The concentration of the prostaglandin analog throughout the solutions must be uniform. Upon shaking, the concentration of the prostaglandin analog throughout the emulsions and suspensions must be uniform.

The concentration of the prostaglandin analog is adjusted so that a teaspoonful (5 ml.), a tablespoonful (½ ounce or 15 ml.) or a fraction or multiple thereof, will provide an effective amount to produce the desired pharmacological effect. The exact dose depends on the age, weight, and condition of the patient or animal as is known in the art.

The liquid oral dosage forms may be packaged, for example, in unit-dose sizes of 5 ml. (teaspoonful), 10 ml., 15 ml. (tablespoonful) and 30 ml. (one ounce), and multiple dose containers, including, for example, 2 oz., 3 oz., 4 oz., 6 oz., 8 oz., pint, quart, and gallon sizes.

Non-effervescent granules are packaged in predetermined amounts such that when reconstituted with a specified quantity of an appropriate liquid vehicle, usually distilled water, a solution and/or suspension results providing a uniform concentration of the prostaglandin analog after shaking, if necessary. The concentration of the solution is such that a teaspoonful (5 ml.), a tablespoonful (½ ounce or 15 ml.) or a fraction or multiple thereof will provide an effective amount to produce the desired pharmacological effect. The exact dose depends on the age, weight and condition of the patient or animal as is known in the art.

Effervescent granules are packaged either in unit-dose, for example, metal foil packets or in bulk, for example, in 4 oz. and 8 oz. amounts such that a specific amount, either a unit-dose or for example, a teaspoonful, tablespoonful or a fraction or multiple thereof of bulk granules when added to a specific amount of liquid vehicle, for example, water yields a container of liquid dosage form to be ingested. The concentration of the prostaglandin analog in the granules is adjusted so that a specified amount when mixed with a specific amount of water yields an effective amount of prostaglandin analog to produce the desired pharmacological effect. The exact amount of granules to be used depends on age, weight, and condition of the patient as is known in the art.

The pharmaceutically therapeutically active compounds are administered orally or parenterally in unit-dosage forms or multiple-dosage forms. Unit-dose forms as used in the specification and claims refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes (parenteral) individually packaged tablet or capsule (oral-solid) or individually packaged teaspoonful or tablespoonful (oral-liquid). Unit-dose forms may be administered in fractions or multiples thereof. A multiple-dose form is a plurality of identical unit-dosage forms packaged in a single container to be administered in segregrated unit-dose form. Examples of multiple-dose forms include vials (parenteral), bottles of tablets or capsules (oral-solid) or bottles of pints or gallons (oral-liquid). Hence, multiple dose form is a multiple of unit-dose which are not segregated in packaging. The specifications for the unit-dosage form and the multiple-dosage form are dictated by and directly dependent on (a) the unique characteristics of the therapeutically active compound and the particular therapeutic effect to be achieved and (b) the limitations inherent in the art of compounding such a therapeutically active compound.

As indicated, an embodiment of the present invention relates to a method for alleviating a hyporeactive interferon response in interferon-producing human or animal cells having a hyporeactive interferon response which comprises administering to said cells an effective amount of an HIS-PG to alleviate said hyporeactive state. For this purpose a wide variety of dosage schedules can be employed. The dosage schedule for the HIS-PG in accord with this embodiment of the present invention will depend upon a variety of factors, including the type (e.g., foreskin fibroblast and leukocytes), age, and physical condition of the interferon producing human or animal cells, the nature and dosage regimen of interferon inducers being utilized. The particular in vitro method of interferon production employed, the relative ability of the cells (cell cultures) to respond to interferon induction, and the particular HIS-PG to be administered will also influence dosage regimens.

Effective in vitro dosage of the HIS-PG depends upon the potency of the particular HIS-PG relative to $PGE_1$ for which doses in the range of about 5 μg./ml. to about 0.01 μg/ml., more particularly about 1 μg/ml. to about 0.05 μg/ml., can be employed for alleviating the hyporeactive interferon response of the interferon producing cells by direct addition to the culture media.

Further, the dose of HIS-PG which can be used with a given type of hyporeactive human or animal cell capable of producing interferon in an in vitro interferon production process, can be determined utilizing a curve representing the response in quantity of interferon produced as a function of the HIS-PG dose can first be prepared, and the optimum HIS-PG dose deduced therefrom. The production or harvesting of interferon from in vitro production processes is well know in the art.

PROCEDURE I

Determination of Hyporeactive Interferon Stimulating Prostaglandins (HIS-PG's) Utilizing Standard Laboratory Animals The ability of prostaglandin-type compounds to alleviate a hyporeactive interferon response can be readily evaluated in intact animals. Any interferon producing animal can be utilized, however for convenience mice serve as convenient laboratory animals.

Mice are infected intraperitoneally with a 100% lethal inoculum (1000 PFU) of encephalomyocariditis (EMC) virus to render the mice hyporeactive to interferon induction, see D. A. Stringfellow and L. A. Glasgow, Inf. Imm. 6, 743, 1972. At 72 to 96 hours after infection 10 mice groups are injected by any of several routes, most often intraperitoneally, with the particular prostaglandin-type compound at varying doses per group in the range of 5 mg./kg. to 0.01 mg./kg., for example 5 groups can be utilized at doses 5 mg./kg., 2.5 mg./kg., 1 mg./kg., 0.5 mg./kg. or 0.01 mg./kg. using 10 mice/group. Although various prostaglandins have been active when administered from 4 hours before to four hours after inducer injection, the following serves as a convenient way of identifying active prostaglandins, i.e., HIS-PG's. Each group is divided into 2 equal subgroups of 5 mice each. A suitable interferon inducer, i.e., tilorone HCl (250 mg./kg. PO) is administered to one 5 mouse subgroup immediately following the injection of the prostaglandin-type compound and the other 5 mouse/group receive inducer 1 hour subsequent to the injection of the prostaglandin type compound. One hour prior to injection of the prostaglandin-type compound another 5 mice also receive orally 250 mg./kg. tilorone HCl. At the time of maximum interferon response (18–24 hours post tilorone HCl administration) the mice are bled, the serum collected and pooled per 5 mice/group and the pooled serum assayed for interferon using a standard plaque reduction assay, see Finter, Inter-feron assays and standards, in Interferons ed. by N. B. Finter, W. B. Saunders Co., Phil. PA. pp. 89–120 (1966). In each evaluation, controls consist of EMC infected mice injected with interferon inducer (tilorone HCl) but not treated with a prostaglandin-type compound and EMC infected mice treated with prostaglandin but not receiving inducer. The interferon response of these mice serve as controls against which the prostaglandin-type compound treated mice are compared. An enchancement of >50% of the EMC infected control group that received no prostaglandin is considered significant. In each evaluation, $PGE_1$ at the same dosage levels, including 1 mg./kg., as the prostaglandin-type compound being evaluated is also included as a positive control.

The following methods describe the manner and process of using this invention and are to be construed as exemplary embodiments of the invention concept and not as limitations thereof.

EXAMPLE 1

$PGE_1$ is administered parenterally at a dosage of 0.1 mg./kg. given over a time span of 30 minutes to a human suffering from a hyporeactive interferon response following administration of polyriboinosinic-polyribocytidylic acid (Poly I:C).

EXAMPLE 2

$PGE_1$ is administered parenterally at a dosage of 0.01 mg./kg. given over a time span of 30 minutes to a human suffering from a hyporeactive interferon response following administration of polyriboinosinic-polyribocytidylic acid (Poly I:C).

EXAMPLE 3

$PGE_1$ is administered parenterally at a dosage of 0.001 mg./kg. given over a time span of 30 minutes to a human suffering from a hyporeactive interferon response following administration of polyriboinosinic-polyribocytidylic acid (Poly I:C).

EXAMPLE 4

$PGE_1$ is administered orally at a dosage of 0.2 mg./kg. (divided among 3 doses over 8 hours) to a human suffering from a hyporeactive interferon response.

EXAMPLE 5

$PGE_1$ is administered parenterally at a dosage of 0.1 mg./kg. given over a time span of 30 minutes to a human suffering from a hyporeactive interferon response resulting from an infection with cytomegalovirus.

EXAMPLE 6

$PGE_1$ is administered parenterally at a dosage of 0.01 mg./kg. given over a time span of 30 minutes to a human suffering from a hyporeactive interferon response resulting from an infection with cytomegalovirus.

EXAMPLE 7

$PGE_1$ is administered parenterally at a dosage of 0.001 mg./kg. given over a time span of 30 minutes to a human suffering from a hyporeactive interferon response resulting from an infection with cytomegalovirus.

It should be noted that under certain conditions the ability of HIS-PG's to alleviate hyporeactivity to interferon induction might be limited. This is particularly true in animals rendered hyporeactive by multiple doses of specific non-viral interferon inducers. However, limited effectiveness in the use of therapeutic agents is not novel, for example, it is known that L-dopa is effective in the treatment of Parkinson's disease in some and non-effective in others.

To date, the evaluation of the ability of particular HIS-PG's to alleviate hyporeactivity to interferon induction has generally produced favorable but occasionally unfavorable results in laboratory experiments involving the restoration of interferon responsiveness in hyporeactive mice and hyporeactive cell cultures.

It is believed that part of the hyporeactivity to interferon induction that develops following repeated levels of an inducer is apparently mediated by specific interferon inducers overloading the ability of cells to respond to interferon induction. For example, mice rendered hyporeactive by a single oral dose of tilorone HCl (250 mg./kg.) are generally hyporeactive to interferon induction of a second dose of the same inducer given 24–72 hours later. HIS-PG's administered prior to or subsequent to the second dose do not appear to be capable of overcoming the hyporeactive state. This inability to overcome the hyporeactive state is believed partly due to high levels of inducer circulating and being deposited throughout the reticuloendothial system for 72–96 hours after administration. However, other interferon inducers, for example Poly I:C, are more labile and do not seem to overload the cell or animal and are more ameniable to restoration of interferon responsiveness by HIS-PG's.

I claim:

1. A method for alleviating hyporeactivity to interferon induction in interferon-producing animals or animal cells having a hyporeactive interferon response which comprises administering to said animal or animal cells an effective amount of a hyporeactive interferon stimulating prostaglandin (HIS-PG) to alleviate said hyporeactive response.

2. The method according to claim 1 wherein the HIS-PG is selected from the group consisting of A-type prostaglandins, E-type prostaglandins, F-type prostaglandins and D-type prostaglandins effective to increase the interferon response in animals or animal cells having a hyporeactive interferon response.

3. The method according to claim 2 wherein the HIS-PG is $PGE_1$.

4. The method according to claim 2 wherein the HIS-PG is $PGF_1\alpha$.

5. The method according to claim 2 wherein the HIS-PG is $PGA_1$.

6. The method according to claim 2 wherein the HIS-PG is $PGE_2$.

7. The method according to claim 2 wherein the HIS-PG is $PGF_2\alpha$.

8. The method according to claim 2 wherein the HIS-PG is $PGA_2$.

9. The method according to claim 2 wherein the HIS-PG is cis 4,5-didehydro-15-methyl-$PGE_1$ methyl ester.

10. A method for alleviating a hyporeactive interferon response in interferon-producing animals having a hyporeactive interferon response which comprises administering to said animal an effective amount of a hyporeactive interferon stimulating prostaglandin (HIS-PG), in combination with a pharmaceutical carrier, to alleviate said hyporeactive response.

11. The method according to claim 10 wherein the HIS-PG is selected from the group consisting of A-type prostaglandins, E-type prostaglandins, F-type prostaglandins, and D-type prostaglandins effective to increase the interferon response in animals having a hyporeactive interferon response.

12. The method according to claim 10 wherein the animal is a human.

13. The method according to claim 11 wherein the animal is a human.

14. The method according to claim 11 wherein the hyporeactive interferon response is a consequence of administration of an interferon inducer to the interferon-producing animal.

15. The method according to claim 11 wherein the hyporeactive interferon response is a consequence of viral infection in the interferon-producing animal.

16. The method according to claim 11 wherein the hyporeactive interferon response is a consequence of a neoplasia in the interferon-producing animal.

17. The method according to claim 11 wherein the HIS-PG is a A-type prostaglandin.

18. The method according to claim 11 wherein the HIS-PG is an E-type prostaglandin.

19. The method according to claim 11 wherein the HIS-PG is a F-type prostaglandin.

20. The method according to claim 11 wherein the HIS-PG is a D-type prostaglandin.

21. The method according to claim 11 wherein the HIS-PG is $PGE_1$.

22. The method according to claim 11 wherein the HIS-PG is $PGF_1\alpha$.

23. The method according to claim 11 wherein the HIS-PG is $PGA_1$.

24. The method according to claim 11 wherein the HIS-PG is $PGE_2$.

25. The method according to claim 11 wherein the HIS-PG is $PGE_2\alpha$.

26. The method according to claim 11 wherein the HIS-PG is $PGA_2$.

27. The method according to claim 11 wherein the HIS-PG is cis 4,5-dihydro-15-methyl-$PGE_1$ methyl ester.

28. The method according to claim 11 wherein the animal is a human and the HIS-PG is $PGE_1$.

29. The method according to claim 11 wherein the animal is a human and the HIS-PG is $PGF_1\alpha$.

30. The method according to claim 11 wherein the animal is a human and the HIS-PG is $PGA_1$.

31. The method according to claim 11 wherein the animal is a human and the HIS-PG is $PGE_2$.

32. The method according to claim 11 wherein the animal is a human and the HIS-PG is $PGF_2\alpha$.

33. The method according to claim 11 wherein the animal is a human and the HIS-PG is $PGA_2$.

34. The method according to claim 11 wherein the animal is a human and the HIS-PG is cis 4,5-didehydro-15-methyl-$PGE_1$ methyl ester.

35. A method for alleviating a hyporeactive interferon response in interferon-producing human or animal cells having a hyporeactive interferon response which comprises administering to said human or animal cells an effective amount of a hyporeactive interferon stimulating prostaglandin (HIS-PG) to alleviate said hyporeactive response.

* * * * *